(12) United States Patent
Van Egmond et al.

(10) Patent No.: US 7,547,814 B2
(45) Date of Patent: Jun. 16, 2009

(54) SEPARATION OF OLEFIN VAPOR FROM LIQUID FRACTION TO REDUCE FOULING

(75) Inventors: Cor F. Van Egmond, Pasadena, TX (US); Michael J. Veraa, Houston, TX (US); Steven E. Silverberg, Seabrook, TX (US); Michael P. Nicoletti, Houston, TX (US); John Richard Shutt, Merchtem (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 383 days.

(21) Appl. No.: 11/701,790

(22) Filed: Feb. 2, 2007

(65) Prior Publication Data

US 2008/0185338 A1  Aug. 7, 2008

(51) Int. Cl.
*C07C 7/10* (2006.01)
(52) U.S. Cl. ........................ 585/809; 585/833; 585/867; 585/910; 208/48 Q

(58) Field of Classification Search .................. None
See application file for complete search history.

(56) References Cited

U.S. PATENT DOCUMENTS

| 6,459,009 | B1 | 10/2002 | Miller et al. |
| 6,740,791 | B2 | 5/2004 | Kuechler et al. |
| 7,323,612 | B2 * | 1/2008 | Egmond et al. ............. 585/809 |
| 2006/0047175 | A1 | 3/2006 | Egmond et al. |

* cited by examiner

*Primary Examiner*—Tam M Nguyen

(57) ABSTRACT

This invention is directed to methods of removing water and other condensable materials, as well as solids particles such as catalyst particles, from olefin product streams so as to reduce fouling in the liquid and vapor separation equipment. In order to reduce fouling or contamination in the condensing or quenching process, this invention includes adding a hydrocarbon to at least a portion of the condensed liquid fraction in an amount that effects separation of the liquid fraction into upper and lower fractions.

21 Claims, 2 Drawing Sheets

US 7,547,814 B2

SEPARATION OF OLEFIN VAPOR FROM LIQUID FRACTION TO REDUCE FOULING

FIELD OF THE INVENTION

This invention concerns a process for separating liquid fraction from an olefin stream to reduce fouling. In particular, this invention concerns separating liquid fractions from an olefin feed produced from an oxygenate feed.

BACKGROUND OF THE INVENTION

Light olefins such as ethylene, propylene and butylene serve as feeds for the production of numerous important chemicals and polymers. Typically, light olefins are produced by cracking petroleum feeds.

An alternative route for manufacturing light olefins is to catalytically convert oxygenates such as methanol to an olefin product. This conversion can be accomplished using a variety of molecular sieve catalysts. Several of these catalysts are highly selective in forming ethylene and propylene. However, a significant amount of water is formed as a natural by-product, and this water must be removed from the desired light olefin product.

U.S. Pat. No. 6,740,791 B2 discloses a process for converting an oxygenate to an olefin product. Water is removed from the olefin product using a quench tower to cool the product and condense the water. The olefin portion of the olefin product is recovered in an overhead stream from the quench tower, and the condensed water fraction is recovered as a bottoms stream. The condensed water fraction is recovered from the quench tower, and sent to a fractionator for separation into further streams.

U.S. Pat. No. 6,459,009 B1 discloses an alternative process for converting an oxygenate to an olefin product. Water is removed from the olefin product using a two-stage quench tower to cool the product and condense the water. The olefin product is passed to a first stage quench tower and contacted with an aqueous stream and a neutralizing agent introduced at the top of the quench tower to provide a hydrocarbon vapor stream and a first stage bottoms stream containing water. The vapor stream is cooled and sent to a second stage tower to further separate light olefins and additional water. A portion of the first stage bottoms stream is withdrawn as a drag stream, and another portion of the first stage bottoms stream is recycled to the first stage tower.

U.S. Patent Publication No. 2006/0047175 discloses condensing and removing water and heavy hydrocarbons from an olefin stream containing light olefin compounds such as ethylene, propylene and butylene, and recovering the light olefin compounds. The olefin stream is cooled such that a substantial portion of the water contained in the olefin stream is condensed to form a liquid water stream. Condensation is carried out in a vessel, and following condensation, an olefin vapor stream, the liquid water stream and a hydrocarbon stream are removed from the vessel. The olefin vapor stream that is removed from the vessel is preferably a light olefin stream, preferably comprising one or more olefins selected from the group consisting of ethylene, propylene and butylene.

Removing water and other condensable materials, including catalyst particles that may be present in the olefin product, from an olefin stream can be problematic. Water and catalyst particles are particularly difficult to remove, since hydrocarbon by-product oil is also present and this oil has a tendency to adsorb onto the catalyst particle surface. Although the catalyst particles have a density higher than water, the adsorption of the oil onto the catalyst surface makes the catalyst particles much more difficult to separate from the water, particularly if the oil does not form a clearly separate layer from the water layer, which is often the case. This adsorption of oil on catalyst particles and poor separation of oil and water layers can cause further problems in downstream processing, including increased fouling of equipment and enhanced problems in wastewater treatment.

More efficient systems and methods for separating the condensable materials from the light olefin compounds are desirable. Such systems should be low in maintenance and easy to operate. There is, therefore, a need to pursue more efficient ways of removing water and other condensable materials from olefin streams, particularly olefin streams high in light olefin content.

SUMMARY OF THE INVENTION

This invention provides more efficient ways of removing water and other condensable materials from olefin streams. In particular, this invention provides methods for reducing fouling in these systems.

According to one aspect of the invention, there is provided a process for separating liquid fractions from an olefin stream which can be produced by contacting an oxygenate feed with a molecular sieve catalyst to form the olefin stream. A portion of the olefin stream is condensed to form a liquid fraction (the condensed liquid). Hydrocarbon is added to at least a portion of the liquid fraction in an amount that effects separation of the liquid fraction into an upper and lower fraction. This addition of hydrocarbon facilitates separation of the upper fraction from the lower fraction, and contributes to solid particles being more readily absorbed into the lower liquid fraction, which contains predominantly water, and preferably, a majority of the water separated from the liquid fraction.

In one embodiment, the hydrocarbon has a specific gravity less than that of toluene. In another, the hydrocarbon comprises one or more $C_8$ to $C_{18}$ hydrocarbons. In still another, the hydrocarbon has a surface tension of no greater than 28 dynes/cm at 25° C. Preferably, the hydrocarbon has an initial boiling point of not less than 90° C. It is also preferred that the hydrocarbon has a final boiling point of not greater than 220° C.

In yet another embodiment of the invention, the hydrocarbon comprises no greater than 50 wt % aromatics. In still another, the hydrocarbon has an aniline point of at least 30° C., wherein the aniline point is determined by ASTM D-611. In another, the hydrocarbon comprises at least 1 wt % paraffin.

The condensed liquid fraction typically contains particulate solids, e.g., particles of the molecular sieve catalyst. The addition of the hydrocarbon causes at least a majority of the particles of the molecular sieve catalyst to separate with the lower liquid fraction, which preferably is a water fraction. In one embodiment, the hydrocarbon is added to maintain a concentration of from 0.3 wt % to 30 wt % in the liquid fraction.

In one embodiment of the invention, at least a portion of the liquid fraction (i.e. the condensed liquid) is sent to a separator vessel and the hydrocarbon is added to the portion sent to the separator vessel. Alternatively, the condensing is carried out in a quench vessel and hydrocarbon is added to the quench vessel.

According to another aspect of the invention, a portion of the olefin stream is condensed to form an olefin vapor and a condensed liquid, wherein the liquid fraction comprises water and molecular sieve catalyst particles. The olefin vapor is separated from the condensed liquid and hydrocarbon is added to at least a portion of the condensed liquid to effect separation of the condensed liquid into at least an upper fraction and a lower fraction so the lower fraction contains a majority of the water and the molecular sieve catalyst particles present in the condensed liquid.

BRIEF DESCRIPTION OF THE DRAWINGS

Examples of the invention are provided with reference to the attached Figures, wherein.

DETAILED DESCRIPTION OF THE INVENTION

Figure 1:
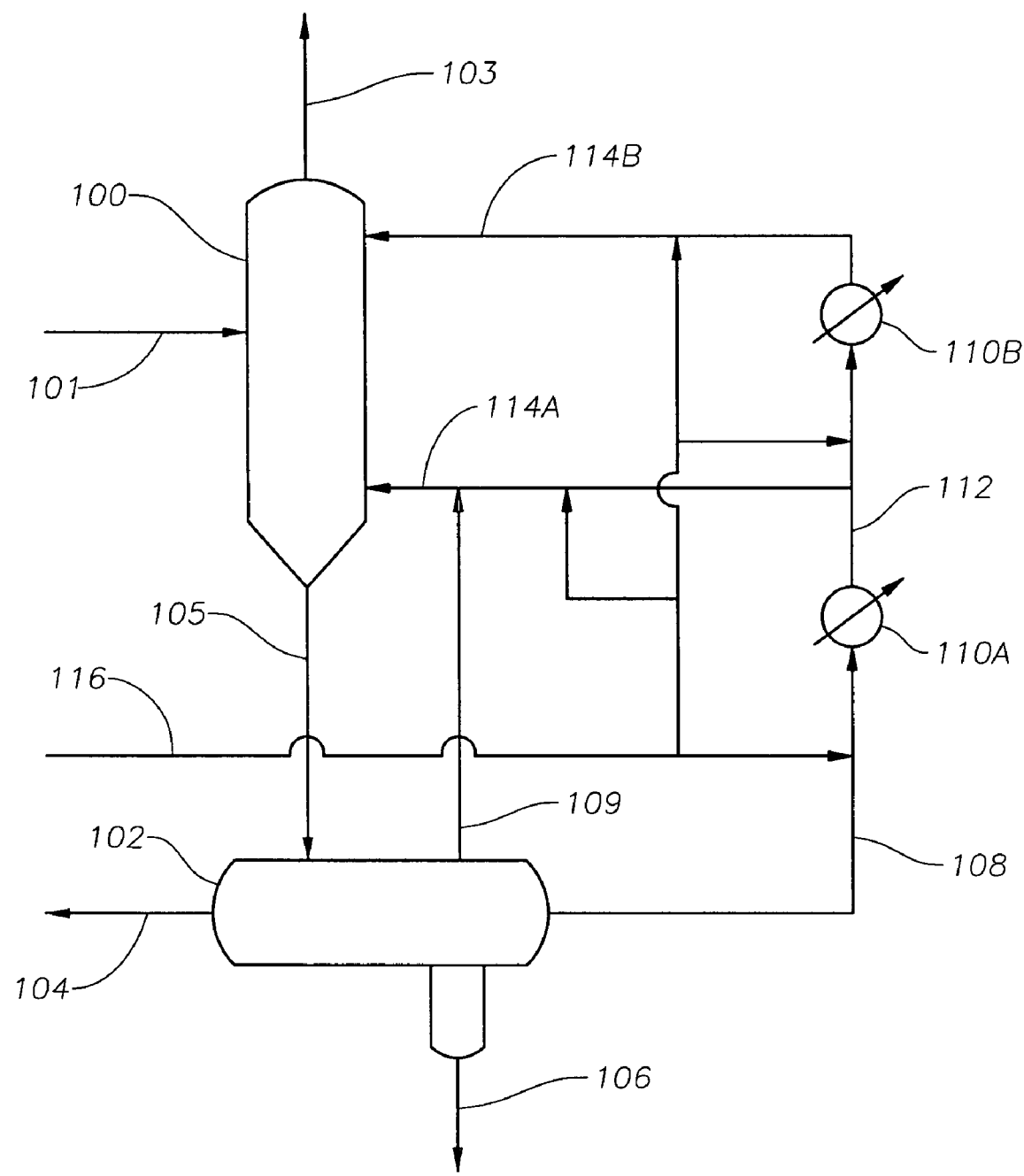
FIG. 1 shows a flow diagram of a preferred embodiment of the invention in which hydrocarbon is injected into a liquid fraction to effect separation of the fraction into upper and lower fractions.

I. Separation of Olefin Vapor from Liquid Fraction to Reduce Fouling

This invention is to a process for separating olefin from higher boiling point hydrocarbons and water, which are all contained in a provided olefin product stream. The process is particularly beneficial in separating out solids particles that can also be entrained in the product stream. The separation process is carried out such that there is relatively low fouling of separation equipment.

The process includes condensing at least a portion of the hydrocarbon and water in the provided olefin product stream to form separate upper and lower liquid fractions. Preferably, at least a majority (i.e., 50%) of the solids in the provided olefin product stream separates with or is collected with the lower liquid fraction, which is also the water fraction.

The invention is particularly advantageous in separating olefin fractions from an olefin stream produced from an oxygenate feed. In such streams, the olefin product typically contains, not only olefin, but can contain at least 30 wt %, typically at least 40 wt %, and sometimes at least 50 wt % water. The olefin product often includes molecular sieve catalyst particles that carry over with the water and olefin, as well as some non-olefin hydrocarbon contaminants that can also carried in the olefin product stream. This invention enables easier separation of components in the olefin product so that fouling is reduced in the separation equipment.

Olefin is generally separated from the non-olefin products in the olefin stream by condensing at least a majority of the non-olefin components to form a liquid fraction and a vapor fraction. A significant portion of the olefin in the olefin product remains in the vapor fraction. Water and hydrocarbons (saturated and unsaturated) having boiling points similar to water's and higher are also condensed into the liquid fraction. Particulate solids in the olefin product stream, e.g., inorganic oxides such as catalyst particles, typically accumulate in the liquid stream. In order to reduce fouling or contamination in the condensing or quenching process, this invention includes adding a hydrocarbon to at least a portion of the liquid fraction in an amount that effects separation of the liquid fraction into upper and lower fractions. The upper fraction is generally hydrocarbon rich, i.e., is comprised of a majority of hydrocarbon components, and the lower fraction is generally water rich, i.e., is comprised of a majority of water. Typically, injection of the hydrocarbon to cause the separation of liquid into at least an upper and a lower fraction also causes the catalyst particles to accumulate in the lower or water fraction, which results in less fouling or contamination of the condensing or quench process.

II. Oxygenate to Olefin Reaction System

In one embodiment of the invention, an olefin stream is obtained by contacting oxygenate with a molecular sieve catalyst. The oxygenate comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol preferably has from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{10}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, ethanol, dimethyl ether, or a mixture thereof.

Molecular sieves capable of converting an oxygenate to an olefin compound include zeolites as well as non-zeolites, and are of the large, medium or small pore type. Small pore molecular sieves are preferred in one embodiment of this invention, however. As defined herein, small pore molecular sieves have a pore size of less than or equal to about 5.0 angstroms. Generally, suitable catalysts have a pore size ranging from about 3.5 to about 5.0 angstroms, preferably from about 4.0 to about 5.0 angstroms, and most preferably from about 4.3 to about 5.0 angstroms.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin forming catalyst capable of producing large quantities of ethylene and propylene is a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5 to about 15 angstroms. Preferred are the small pore SAPO molecular sieves having an average pore size of less than or equal to about 5 angstroms, preferably an average pore size ranging from about 3.5 to about 5 angstroms, more preferably from about 3.5 to about 4.2 angstroms. These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides, which can have an ALPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions.

The metal containing ALPOs have a three-dimensional microporous crystal framework structure of MO$_2$, AlO$_2$ and PO$_2$ tetrahedral units. These as manufactured structures (which contain template prior to calcination) can be represented by empirical chemical composition, on an anhydrous basis, as mR:(M$_x$Al$_y$P$_z$)O$_2$, wherein "R" represents at least one organic templating agent present in the intracrystalline pore system; "m" represents the moles of "R" present per mole of (M$_x$Al$_y$P$_z$)O$_2$ and has a value of from zero to 0.3, the maximum value in each case depending upon the molecular dimensions of the templating agent and the available void volume of the pore system of the particular metal aluminophosphate involved, "x," "y," and "z" represent the mole fractions of the metal "M," (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

Materials can be blended with the molecular sieve to form what is generally referred to as formulated catalyst. Such blended materials can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, and acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 angstroms to about 3,000 angstroms, more preferably from about 30 angstroms to about 200 angstroms, most preferably from about 50 angstroms to about 150 angstroms.

A molecular sieve catalyst particularly useful in making ethylene and propylene is a catalyst, which contains a combination of SAPO-34, and SAPO-18 or ALPO-18 molecular sieve. In a particular embodiment, the molecular sieve is a crystalline intergrowth of SAPO-34, and SAPO-18 or ALPO-18.

To convert oxygenate to olefin, conventional reactor systems can be used, including fixed bed, fluid bed or moving bed systems. Preferred reactors of one embodiment are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 hr$^{-1}$, preferably in the range of from about 1 hr$^{-1}$ to 1000 hr$^{-1}$, more preferably in the range of from about 20 hr$^{-1}$ to about 1000 hr$^{-1}$, and most preferably in the range of from about 50 hr$^{-1}$ to about 500 hr$^{-1}$. WHSV is defined herein as the weight of oxygenate, and reactive hydrocarbon which may optionally be in the feed, per hour per weight of the molecular sieve in the reactor. Because the catalyst or the feedstock may contain other materials which act as inerts or diluents, the WHSV is calculated on the weight basis of the oxygenate feed, and any reactive hydrocarbon which may be present with the oxygenate feed, and the molecular sieve contained in the reactor.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow with a relatively high content of oxygenated olefin by-products being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPa), preferably at least about 5 psia (34 kPa). The process is particularly effective at higher total pressures, including a total pressure of at least about 20 psia (138 kPa). Preferably, the total pressure is at least about 25 psia (172 kPa), more preferably at least about 30 psia (207 kPa). For practical design purposes it is desirable to use methanol as the primary oxygenate feed component, and operate the reactor at a pressure of not greater than about 500 psia (3445 kPa), preferably not greater than about 400 psia (2756 kPa), most preferably not greater than about 300 psia (2067 kPa).

Undesirable by-products can be avoided by operating at an appropriate gas superficial velocity. As the gas superficial velocity increases the conversion decreases avoiding undesirable by-products. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation depends on the total number of moles of gas present and the cross section of a particular location in the reaction zone, temperature, pressure and other relevant reaction parameters.

In one embodiment, the gas superficial velocity is maintained at a rate of greater than 1 meter per second (m/s) at least one point in the reaction zone. In another embodiment, it is desirable that the gas superficial velocity is greater than about 2 m/s at least one point in the reaction zone. More desirably, the gas superficial velocity is greater than about 2.5 m/s at least one point in the reaction zone. Even more desirably, the gas superficial velocity is greater than about 4 m/s at least one point in the reaction zone. Most desirably, the gas superficial velocity is greater than about 8 m/s at least one point in the reaction zone.

III. Removing Water and Solid from the Olefin Product

The oxygenate to olefin process forms a substantial amount of water as a by-product. Much of this water by-product can be removed from the olefin product of the oxygenate to olefin process by cooling the olefin product and condensing at least a portion of the product to form an olefin vapor stream and a condensed, liquid stream, with the condensed stream containing a substantial amount of water. This condensed stream will also typically contain hydrocarbons that have an atmospheric boiling point higher than that of the olefin vapor stream.

The condensed liquid stream will also generally contain solid material, such as catalyst particles carried over from the reaction process. This invention provides a way to remove the hydrocarbon and solid particles from the condensed liquid stream so as to minimize fouling in the condensation or quench system. This is done by injecting a hydrocarbon into the condensed liquid in an amount that effects separation of the condensed liquid into at least a hydrocarbon-containing layer and a water-containing layer. The hydrocarbon layer will typically form as an upper fraction and the water layer will typically form as a lower fraction. Then the two fractions can be more easily separated, with the solids particles less likely to "stick" onto or foul the quench system. In general, the solids particles tend to separate with the water layer, and the water layer can be sent to additional hydrocarbon or solid separation equipment or on to waste water treatment. The separated hydrocarbon can be recycled back into the oxygenate-to-olefin conversion process, if desired.

Preferably, the olefin product from the oxygenate to olefin process is cooled to a temperature below the condensation temperature of the condensation temperature of the water vapor in the stream in order to condense the undesirable by-products. More particularly, the temperature of the olefin product stream is cooled to a temperature below the condensation temperature of the oxygenate feed used in the oxygenate to olefin process. In certain embodiments, the olefin product is cooled below the condensation temperature of ethanol, and in certain embodiments below that of methanol.

Upon condensation, a liquid stream is formed that is rich in water by-product. The vapor stream that remains following condensation is rich in olefins, particularly the light olefins (e.g., one or more of ethylene, propylene and butylene).

According to one embodiment of the invention, at least a portion of the olefin product stream containing water, olefin and other hydrocarbon is condensed to form a liquid fraction. Hydrocarbon is added to at least a portion of the liquid fraction in an amount to effect separation of the liquid fraction into an upper and lower fraction. The upper fraction is then separated from the lower fraction.

The hydrocarbon that is added preferably has a specific gravity less than that of toluene. In particular, the hydrocarbon that is added preferably has a specific gravity of no greater than 0.85 at 15.5° C./15.5° C. More preferably, the hydrocarbon has a specific gravity of no greater than 0.8 at 15.5° C./15.5° C., most preferably no greater than 0.75 at 15.5° C./15.5° C.

It is also preferred that the added hydrocarbon comprise one or more $C_8$ to $C_{18}$ hydrocarbons. Preferably, the added hydrocarbon comprises one or more $C_{11}$ to $C_{16}$ hydrocarbons, more preferably at least a majority (i.e., 50 wt %) of $C_{12}$ hydrocarbons.

According to another embodiment the hydrocarbon has a surface tension less than that of toluene. In one embodiment, the hydrocarbon has a surface tension of no greater than 28 dynes/cm at 25° C. Preferably, the hydrocarbon has a surface tension of no greater than 26 dynes/cm at 25° C., most preferably no greater than 24 dynes/cm at 25° C.

The hydrocarbon should also have a boiling point that is not so low that it evaporates with the olefin vapor or adversely affects the separation of the hydrocarbon and water layers. Preferably, the hydrocarbon has an initial boiling point of not less than 90° C. (with all boiling points referred to herein meaning boiling point at 1 atm., and boiling points of mixtures preferably being determined according to ASTM D-86). More preferably, the hydrocarbon has an initial boiling point of not less than 95° C., most preferably not less than 100° C. It is also preferred that the hydrocarbon has a final boiling point of not greater than 220° C., more preferably a final boiling point of not greater than 210° C., and most preferably not greater than 205° C.

In one embodiment, the hydrocarbon comprises no greater than 50 wt % aromatics. Preferably, the hydrocarbon comprises no greater than 20 aromatics, more preferably no greater than 10 wt % aromatics.

In another embodiment, the hydrocarbon has an aniline point of at least 30° C., wherein the aniline point is determined by ASTM D-611. Preferably, the hydrocarbon has an aniline point of at least 40° C., more preferably an aniline point of at least 50° C.

In an alternative embodiment, the hydrocarbon comprises at least 1 wt % paraffin (with all wt % referred to herein meaning wt % based on total weight of the hydrocarbon being added). Preferably, the hydrocarbon comprises at least 10 wt % paraffin, more preferably at least 30 wt % paraffin, still more preferably at least 40 wt % paraffin, and most preferably at least 60 wt % paraffin. The paraffin can be linear, branched or a mixture of linear and branched. Preferably, the hydrocarbon is comprised of a majority of branched paraffins (i.e., isoparaffins).

In another alternative embodiment, the hydrocarbon comprises at least 1 wt % naphthenics. Preferably, the hydrocarbon comprises from 1 wt % to 70 wt % naphthenics, more preferably from 1 wt % to 50 wt %, and most preferably from 1 wt % to 30 wt %.

In some embodiments, the hydrocarbon comprises olefins. In such embodiments, high concentrations of olefins are desirable. In one embodiment, the hydrocarbon comprises greater than 50 wt % olefins. Preferably, the hydrocarbon comprises at least 80 wt % olefins, more preferably at least 90 wt % olefins.

The hydrocarbon is added to the liquid fraction in sufficient amount to effect or increase separation of the liquid fraction into at least upper and lower fractions. Preferably, the hydrocarbon is added to maintain a concentration of from 0.3 wt % to 30 wt % in the liquid fraction (i.e., total weight of the liquid fraction after addition of the hydrocarbon). More preferably, the hydrocarbon is added to maintain a concentration of from 0.5 wt % to 15 wt % in the liquid fraction, most preferably of from 1 wt % to 10 wt %.

The olefin vapor stream that is removed following condensation typically contains at least 50 wt % total olefin, based on total weight of the vapor stream. Preferably, the olefin vapor stream that is removed following condensation contains at least 60 wt %, more preferably at least 70 wt %, and most preferably at least 80 wt % total olefin, based on total weight of the vapor stream.

The olefin vapor stream that is removed following condensation is also low in water content. In one embodiment, the olefin vapor stream contains not greater than about 20 wt % water, preferably not greater than about 15 wt % water, more preferably not greater than about 12 wt % water.

In one embodiment, the condensed liquid fraction is condensed in a quench system. The quench system comprises at least one quench vessel and a pumparound system in fluid connection with the quench vessel. The pumparound system comprises at least one pump and at least one cooling vessel. A settler or separator vessel can also be included in the pumparound system. The hydrocarbon can be injected into the quench vessel, the pumparound system or both. The upper and lower layers can, therefore, be formed in the quench vessel or pumparound system. In one embodiment, at least a portion of the condensed liquid fraction is sent from the quench vessel to a separator vessel, and the hydrocarbon is added to the portion sent to the separator vessel. In another embodiment, the condensing is carried out in a quench vessel and hydrocarbon is added directly to the quench vessel.

EXAMPLES

Example 1

Olefin product was obtained from a methanol-to-olefins reaction system, which used SAPO catalyst in the reaction system. The olefin product contained light olefin, water and catalyst particles. The olefin product was sent to a quench system such as that shown in FIG. 1. The quench system included a quench column 100, where light olefins and other light components were removed through a line 103 and a liquid stream containing the catalyst particles were removed by way of a line 105 and sent to a settler 102. A portion of the liquid stream was sent from settler 102 through a line 108 to cooler 110A. A stream from settler 102 was also sent through line 109 back to quench column 100 by way of a line 114A.

A portion of the liquid from line 112 was sent back to quench column 100 by way of a line 114A, and a portion to cooler 110B. From cooler 110B liquid was sent through line 114B to quench column 100. A portion of the liquid stream was also sent from settler 102 through line 106, and ultimately to a wastewater treatment system.

No treatment of the quench system was provided. The coolers 110A and 110B became fouled after a short time of operation.

Samples from lines 108 and 109 were also taken. The appearance of both samples was reported similar—a black oily suspension which on cooling allowed some sedimentation. A sample from line 108 was analyzed.

On standing, the sample gave a supernatant aqueous layer and two different colored sediments. The predominant and lower sediment was black. Above this black layer was a thin layer of gray colored fluffy material. There were only a few drops of oil on the aqueous surface, not a complete layer.

A qualitative gas chromatograph (GC) of the aqueous layer showed several low carbon number oxygenates, primarily methanol, some acetone and acetaldehyde and low levels of $C_3$-$C_5$ alcohols, aldehydes & ketones.

Filtration of the shaken black water sample yielded an aqueous filtrate upon which a few drops of yellow-green oil floated. The filtrand was a soft, black, sticky residue which would not dry on filter paper. This was washed three times with o-xylene yielding a yellow green hydrocarbon phase and a fine black powder. Optical microscopy showed this powder to contain minute, smooth, spheres of fairly uniform size. Thermogravimetric analysis showed 21% wt loss up to 550° C. under argon indicating loss of water and lighter hydrocarbons, 7% weight loss on introduction of air at 580° C. indicating coke burn off and a 72% residue in air at 850° C.

Figure 2:
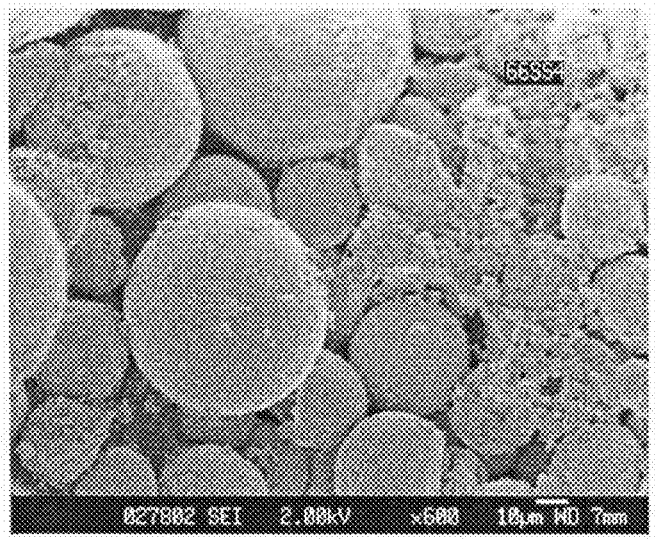
FIG. 2 shows a scanning electron microscopy (SEM) analysis of solid particles mixed together with some debris in the condensed liquid fraction as further described in Example 1.
Figure 3:
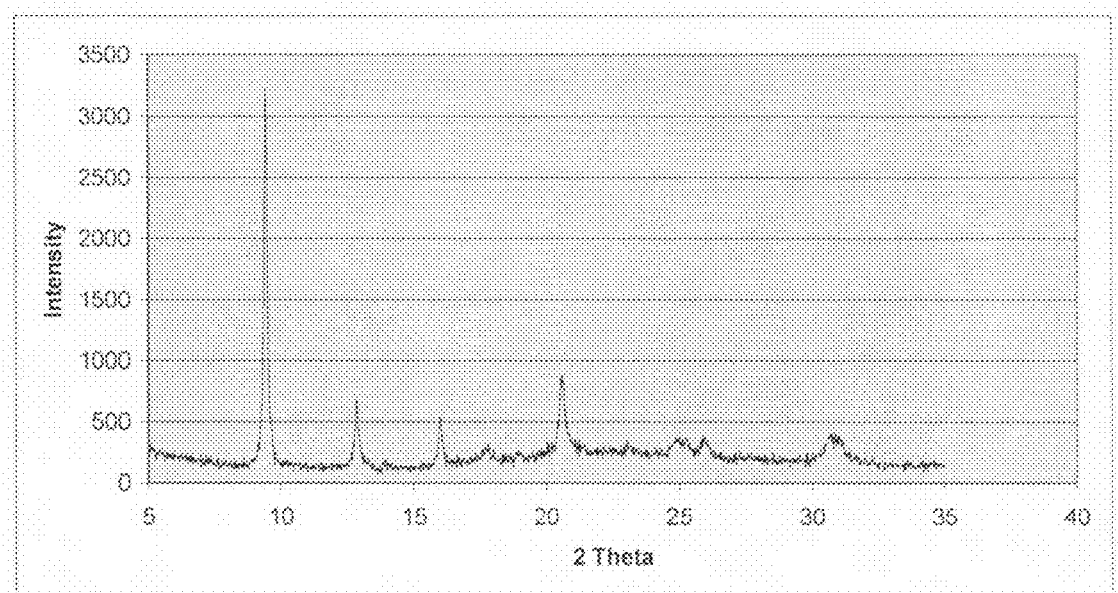
FIG. 3 shows an X-ray diffraction pattern of solid material or particles incorporated into a condensed liquid fraction as further described in Example 1.

Scanning electron microscopy (SEM) analysis of the sample showed spherical particles together with some debris (FIG. 2). The diameter of the spherical particles (SAPO catalyst particles) varied between ~20 μm and ~70 μm. The methanol adsorption capacity of an air calcined sample was determined to be 7 wt % based on total mass. This high number indicates that the solid is still highly crystalline, as confirmed by X-ray diffraction (FIG. 3).

The activity of this sample for methanol conversion to light olefins was determined at 450° C. and about 900 WHSV (sieve based, assuming 40 wt % sieve). A (pseudo) first order rate constant of 42 Hz was determined.

It was surprising that the sample still had X-ray crystallinity as well as activity for methanol conversion. Apparently the SAPO molecular sieve catalyst particles were protected from ambient aging (hydrolysis) by the adsorbed hydrocarbon phase.

These data suggest the recovered solids can be recycled back to the reactor; the particle size range may have an added benefit for the reactor hydrodynamics. Generally, a majority (at least 50%) of the solid particles present can range from 10 µm to 100 µm in diameter.

Qualitative GC-MS analysis of the o-xylene washings showed several hundred, essentially aromatic components between $C_9$ and $C_{24}$. All were heavily alkylated with a few methoxy and phenyl ether groups. Major components were 4C to 6C alkyl benzenes, 3C to 6C alkyl naphthalenes and smaller quantities of many 3+ ring aromatic components.

The sample from line 108 consisted of an aqueous suspension of catalyst particles coated with aromatic oil. The oil to catalyst ratio was such the oil was adsorbed onto the surface of the particles and no separate oil phase was formed.

The highly methylated aromatic oil would have a density in the range 0.90-0.93. The inorganic catalyst particles had a density about 1.5. Oil and water have densities declining with temperature whereas density of particles will remain constant. Thus density—temperature relationship of the oil coated particles should differ markedly from that of water. Sedimentation occurred slowly at room temperature but under process conditions the densities of hot water and the oily coated particles would be closer thus impeding phase separation.

Example 2

In an attempt to alleviate the problem fouling and sediment problems in Example 1, toluene was injected through line 116 and into one or more of the lines shown in FIG. 1. This removed some material from the bottoms circuit, but did not significantly improve the oil-water separation in settler 102.

Example 3

Several potential hydrocarbons were screened for their effectiveness in enhancing the phase separation and decreasing the stickiness of the oily coated particles. Basic properties are summarized in the table below.

TABLE

|  | Isopar C | Isopar J | Tetramer K NDG | ODG bottoms | Exxsol D40 | Varsol 30 | Toluene |
|---|---|---|---|---|---|---|---|
| IBP C | 100 | 185 | 180 | C9 | 159 | 142 | {111} |
| FBP C | 106 | 204 | 202 | C18 | 170 | 164 | {111} |
| sp. grav. @ 15.6/1.6 C. | 0.699 | 0.766 | 0.770 | 0.755 | 0.766 | 0.766 | 0.867 |
| Aniline pt C | 79 | 80 | — | — | 67 | 52 | <20 |
| aromatics wt % | 0 | 0 | 0 | 0 | 0 | 22 | 100 |
| paraffins wt % | 100 | 100 | 0 | 0 | ca. 40 | ca. 40 | 0 |
| naphthenics wt % | 0 | 0 | 2 | 0 | ca. 60 | ca. 40 | 0 |
| Olefins wt % | 0 | 0 | 98 | Ca 100 | 0 | 0 | 0 |
| surface tension | 19 | 24.1 | — | — | 24.5 | 23.9 | 28.5 |
| viscosity | 0.5 | 1.23 | — | — | 0.93 | 0.71 | 0.59 |

The above hydrocarbon streams were considered to be satisfactory solvents for the aromatic oil.

Shaking the black water sample in a glass flask with an aromatic solvent such as toluene or o-xylene was not particularly effective. A separate aromatic phase formed on the surface of the water, but neither fast nor cleanly. In addition the sediment of particles retained a sticky character smearing the glass surface. Decreasing solvent density and aromaticity improved water-hydrocarbon separation efficiency. In addition the particles sediment became cleaner and less sticky.

Isoparaffins such as Isopars and olefin streams such as Tetramer K and ODG bottoms performed quite satisfactorily in both respects.

The relative performance based upon visual observations is:

Isopar C≈Isopar J>Tetramer K>ODG bottoms>Exxsol D40>>Varsol 30>>>toluene

Interestingly clean particles did not readily form a suspension on shaking with a clean paraffinic/olefinic solvent. However shaking the particles with the aqueous phase (water with methanol, acetone etc) readily formed a clean suspension.

Example 4

In another experiment where black water had been treated with toluene producing a poor separation and smearing of the glass surfaces, shaking gently with Isopar J produced a rapid water-hydrocarbon separation, a cleaning of the smeared surfaces and a clear sedimentation of particles.

The role of solvent aromatic and naphthenic content is exemplified by the comparison of Isopar J, Tetramer K, ODG bottoms, Exxsol D40 and Varsol 30, all having essentially the same density. Water-hydrocarbon separation efficiency was fairly similar but the quality of particles sedimentation differed. Isopars and Tetramer K gave clean free flowing particles while ODG bottoms showed limited smearing of particles on the glass. Increasing the naphthenic and especially the aromatic content enhanced the smearing of particles.

If particles are capable of smearing and adhering quite well to a smooth glass surface then the problem will be expected to be more severe on carbon steel.

A desirable characteristic for a process solvent to improve the phase separation is solvency for the aromatic oil yielding a solution with a density much lower than water to force a rapid aqueous-hydrocarbon phase separation. Once the catalyst particles have been cleaned of oil, their 1.5 density allows rapid sedimentation. To ensure good cleaning of the particles while minimizing the volume of the flushing solvent, is it preferred to efficiently solvent with black water.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:

1. A process for separating an olefin stream, comprising: condensing a portion of the olefin stream to form a liquid fraction containing olefin, water, and particulate solids;
adding hydrocarbon to at least a portion of the liquid fraction in an amount to effect separation of the liquid fraction into an upper and lower fraction, the upper fraction containing fewer of the particulate solids than the lower fraction; and
separating the upper fraction from the lower fraction;
wherein the hydrocarbon comprises one or more $C_8$ to $C_{18}$ hydrocarbons; the hydrocarbon has a specific gravity less than that of toluene and has a surface tension of no greater than 28 dynes/cm at 25° C.

2. The process of claim 1, wherein the hydrocarbon has an initial boiling point of not less than 90° C.

3. The process of claim 1, wherein the hydrocarbon has a final boiling point of not greater than 220° C.

4. The process of claim 1, wherein the hydrocarbon comprises no greater than 50 wt % aromatics.

5. The process of claim 1, wherein the hydrocarbon has an aniline point of at least 30° C.

6. The process of claim 1, wherein the hydrocarbon comprises at least 1 wt % paraffin.

7. The process of claim 1, wherein at least a portion of the solid particulates in the condensed liquid fraction are particles of molecular sieve catalyst.

8. The process of claim 7, wherein at least a majority of the particles of the molecular sieve catalyst separate with the lower liquid fraction.

9. The process of claim 8, wherein the lower liquid fraction is a water fraction.

10. The process of claim 1, wherein the hydrocarbon is added to maintain a concentration of from 0.3 wt % to 30 wt % in the liquid fraction.

11. The process of claim 1, wherein at least a portion of the liquid fraction is sent to a separator vessel and the hydrocarbon is added to the portion sent to the separator vessel.

12. The process of claim 1, wherein the condensing is carried out in a quench vessel and hydrocarbon is added to the quench vessel.

13. A process for separating an olefin stream produced from an oxygenate feed into a vapor and liquid fractions, comprising:
contacting the oxygenate feed with a molecular sieve catalyst to form an olefin stream;
condensing a portion of the olefin stream to form an olefin vapor and a condensed liquid, wherein the liquid comprises water and molecular sieve catalyst particles;
separating the olefin from the condensed liquid;
adding hydrocarbon to at least a portion of the condensed liquid to effect separation of the condensed liquid fraction into at least an upper fraction and a lower fraction so the lower fraction contains a majority of the water and the molecular sieve catalyst particles present in the condensed liquid; and
separating the upper fraction from the lower fraction;
wherein the hydrocarbon comprises one or more $C_8$ to $C_{18}$ hydrocarbons; the hydrocarbon has a specific gravity less than that of toluene and has a surface tension of no greater than 28 dynes/cm at 25° C.

14. The process of claim 13, wherein the hydrocarbon has an initial boiling point of not less than 90° C.

15. The process of claim 13, wherein the hydrocarbon has a final boiling point of not greater than 220° C.

16. The process of claim 13, wherein the hydrocarbon comprises no greater than 50 wt % aromatics.

17. The process of claim 13, wherein the hydrocarbon has an aniline point of at least 30° C.

18. The process of claim 13, wherein the hydrocarbon comprises at least 1 wt % paraffin.

19. The process of claim 13, wherein the hydrocarbon is added to maintain a concentration of from 0.3 wt % to 30 wt % in the condensed liquid.

20. The process of claim 13, wherein at least a first portion of the condensed liquid is sent to a separator vessel and the hydrocarbon is added to the first portion.

21. The process of claim 13, wherein the condensing is carried out in a quench vessel and hydrocarbon is added to the quench vessel.

* * * * *